US009952321B2

(12) United States Patent
Fink et al.

(10) Patent No.: US 9,952,321 B2
(45) Date of Patent: Apr. 24, 2018

(54) IMAGING METHOD AND DEVICE USING SHEAR WAVES

(75) Inventors: Mathias Fink, Meudon (FR); Ralph Sinkus, Paris (FR); Mickaël Tanter, Paris (FR); Jeremy Bercoff, Paris (FR)

(73) Assignees: Centre National de la Recherche Scientifique—CNRS, Paris (FR); Universite Paris 7—Denis Diderot 2, Paris (FR)

( * ) Notice: Subject to any disclaimer, the term of this patent is extended or adjusted under 35 U.S.C. 154(b) by 2007 days.

(21) Appl. No.: 11/910,491

(22) PCT Filed: Mar. 30, 2006

(86) PCT No.: PCT/FR2006/000702
§ 371 (c)(1),
(2), (4) Date: Oct. 2, 2007

(87) PCT Pub. No.: WO2006/106213
PCT Pub. Date: Oct. 12, 2006

(65) Prior Publication Data
US 2009/0124901 A1    May 14, 2009

(30) Foreign Application Priority Data

Apr. 5, 2005 (FR) ..................... 05 03376

(51) Int. Cl.
*G01S 15/89* (2006.01)
*A61B 8/08* (2006.01)
*A61B 8/00* (2006.01)
*G01S 7/52* (2006.01)
*A61B 5/00* (2006.01)

(52) U.S. Cl.
CPC ........ *G01S 15/8909* (2013.01); *A61B 5/0051* (2013.01); *A61B 8/0825* (2013.01); *A61B 8/406* (2013.01); *A61B 8/42* (2013.01); *A61B 8/485* (2013.01); *G01S 7/52026* (2013.01)

(58) Field of Classification Search
USPC ...................................................... 600/437
See application file for complete search history.

(56) References Cited

U.S. PATENT DOCUMENTS 5,606,971 A    3/1997 Sarvazyan
5,810,731 A    9/1998 Sarvazyan et al.
(Continued)

FOREIGN PATENT DOCUMENTS

WO    WO 2004/021038 A1    3/2004

OTHER PUBLICATIONS

French Search Report FR 0503376 dated Nov. 16, 2005.
(Continued)

*Primary Examiner* — Katherine Fernandez
(74) *Attorney, Agent, or Firm* — Miller, Matthias & Hull LLP

(57) ABSTRACT

The inventive imaging method consists in generating a mechanical wave having shearing and compressional components in a viscoelastic medium and in determining the movement parameter of said viscoelastic medium at different points during the propagation of said mechanical wave. Said method comprises a correction stage when the movement parameter is processed for eliminating errors caused by the compressional component of the mechanical wave.

11 Claims, 2 Drawing Sheets

(56) References Cited

U.S. PATENT DOCUMENTS

| | | | |
|---|---|---|---|
| 5,855,557 A * | 1/1999 | Lazenby | 600/443 |
| 6,791,901 B1 | 9/2004 | Robertsson et al. | |
| 2004/0204860 A1 | 10/2004 | Ghosh et al. | |
| 2005/0038339 A1 | 2/2005 | Chauhan et al. | |
| 2005/0252295 A1 | 11/2005 | Fink et al. | |

OTHER PUBLICATIONS

International Search Report for parent patent app. PCT/FR2006/000702 dated Jun. 22, 2006.

Tanter—*Ultrafast Compound Imaging for 2-D Motion Vector Estimation: Application to Transient Elastography*, IEEE Transactions on Ultrasonics, Perroelectrics and Frequency Control, vol. 49, No. 10, Oct. 2002.

\* cited by examiner

IMAGING METHOD AND DEVICE USING SHEAR WAVES

CROSS REFERENCE TO RELATED APPLICATION

This is the U.S. National Phase of International Application No. PCT/FR2006/000702filed 30 Mar. 2006, the entire disclosure of which is incorporated herein by reference.

FIELD OF THE DISCLOSURE

The present invention relates to imaging methods and devices using shear waves.

More particularly, the invention relates to an imaging method in which a mechanical wave having a shear component and a compression component is generated in a viscoelastic medium and at least one parameter describing the movement of the viscoelastic medium at various points during the propagation of this mechanical wave is determined.

Thus, a qualitative and/or quantitative analysis may be performed, in particular to identify regions of different hardness from the rest of the viscoelastic medium or regions having a different relaxation time from the rest of the viscoelastic medium.

Document WO-A-04/21038 describes an example of such a method, in which said parameter describing the movement (especially the displacement) in a plane, following the remote generation of a localized pulsed thrust, which creates the mechanical wave in question, in this case a shear wave, is determined.

BACKGROUND OF THE DISCLOSURE

Although this method is already completely satisfactory, the present invention disclosure will further perfect it, so as to improve its precision and, where appropriate, to use it for imaging in three dimensions.

For this purpose, a method of the kind in question is characterized in that it includes a correction step during which the movement parameter is processed so as to remove the effects due to the compression component of said mechanical wave.

Thus, even when a pulsed thrust is used, if the compression component of the elastic mechanical wave that results therefrom disturbs the measurement of the movement parameter, only the effects of the shear component are taken into account. When instead of a pulsed mechanical wave a sustained wave is used, for example in order to carry out a relatively long measurement, such as for three-dimensional imaging, the compression component of the mechanical wave is still present during the time of measuring the movement parameter and it therefore greatly disturbs this measurement. The processing according to the invention makes it possible to eliminate this disturbance and, where appropriate, to map the viscoelastic parameters of the medium in two or three dimensions.

SUMMARY OF THE DISCLOSURE

In preferred embodiments of the method according to the invention, one or more of the following arrangements may optionally be furthermore employed:

a curl of said movement parameter is calculated during said correction step;

the method includes at least one observation step (b) during which the propagation of the mechanical wave at a multitude of points in the viscoelastic medium is observed by echography;

the observation step (b) comprises the following substeps:

(b1) a succession of shots of ultrasonic compression waves (whether focused of not) are transmitted into the viscoelastic medium at a rate of at least ten shots per second by an array of transducers; and (b2) acoustic signals received from the viscoelastic medium, including the echoes generated by the ultrasonic compression waves interacting with the viscoelastic medium, are detected and recorded in real time;

the method furthermore includes at least one processing step (c) during which:

(c1) the successive acoustic signals received from the viscoelastic medium during substep (b2) are processed in order to determine successive propagation images of the mechanical wave; and (c2) said movement parameter of the viscoelastic medium is determined at various points from said successive propagation images;

several successive propagation images of the mechanical wave in the viscoelastic medium are produced along several points of view and these successive images are combined in order to determine a vector value of said movement parameter;

a three-dimensional vector value of said movement parameter is determined;

in order to produce successive propagation images of the mechanical wave along several points of view, an array of ultrasonic transducers (a linear array or any other array, such as a phased array, or a 1.5 D array, a 1.75 D array or else a 2 D matrix of piezoelectric transducers) is used that transmits and detects the ultrasonic compression waves along a transmission/detection direction in an analysis plane and said array is displaced outside the viscoelastic medium, causing said analysis plane to be rotated (these arrangements could optionally be used independently of the previous arrangements, and therefore the subject of the invention is also these arrangements as such);

the array is displaced by moving translationally, without the analysis plane being rotated, and then said array is rotated, causing said analysis plane to be rotated;

the transmission/reception direction of the transducers of the array is varied without rotating the analysis plane, and then said array is rotated, by causing said analysis plane to be rotated;

said movement parameter is chosen from a displacement, a displacement velocity and a stress of the viscoelastic medium;

the method includes a mapping step (d) during which at least one parameter describing the propagation of the shear component of the mechanical wave at at least certain points in the viscoelastic medium is calculated, from a variation of the movement parameter over time, in order in this way to determine a map of said propagation parameter in the viscoelastic medium; and the propagation parameter of the shear wave, which is calculated during the mapping step, is chosen from the velocity of the shear waves, the shear modulus, the Young's modulus, the attenuation of the shear waves, the shear elasticity, the shear viscosity and the mechanical relaxation time, or several of these parameters in the case of an anisotropic medium.

Moreover, the subject of the invention is also an imaging device comprising means for generating, in a viscoelastic medium, a mechanical wave having a shear component and a compression component and means for determining at least one parameter describing the movement of the viscoelastic medium at different points during the propagation of this mechanical wave, characterized in that it includes correction means for processing the movement parameter so as to remove the effects due to the compression component of said mechanical wave In preferred embodiments of the device according to the invention, one or more of the following arrangements may furthermore be optionally employed:

the correction means are designed to calculate a curl of said movement parameter;

the device includes a controlled array of ultrasonic transducers for observing the propagation of the mechanical wave at a multitude of points in the viscoelastic medium by echography;

the device includes means for:

(b1) transmitting a succession of shots of ultrasonic compression waves (whether focused or not) into the viscoelastic medium by said array of transducers at a rate of at least 10 shots per second; and (b2) detecting and recording acoustic signals received from the viscoelastic medium, including the echoes generated by the unfocused ultrasonic compression waves interacting with the reflecting particles of said viscoelastic medium, in real time;

the device includes processing means designed to:

(C1) process the successive acoustic signals received from the viscoelastic medium in order to determine successive propagation images of the mechanical wave; and (C2) determine said movement parameter of the viscoelastic medium at various points in the observation field from said successive propagation images;

the processing means are designed to produce several successive propagation images of the mechanical wave in the viscoelastic medium along several points of view and to combine these successive images for determining a vector value of said movement parameter;

the processing means are designed to determine a three-dimensional vector value of said movement parameter;

the array of transducers transmits and detects the ultrasonic compression waves along a transmission/detection direction in an analysis plane and, to produce the successive propagation images of the mechanical wave along several points of view, the device includes displacement means for displacing said array (a linear array or any other array, such as a phased array, or a 1.5 D array, a 1.75 D array or else a 2 D matrix of piezoelectric transducers) outside the viscoelastic medium, said means being designed to rotate said analysis plane (these arrangements could optionally be used independently of the previous arrangements, and therefore the subject of the invention is also these arrangements as such);

the device includes control means designed to control the displacement means and said control means are designed to displace the array translationally without the analysis plane being rotated, and then to rotate said array, causing said analysis plane to be rotated;

the device includes control means designed to control the displacement means, and said control means are designed to vary the transmission/reception direction of the transducers of the array without either translating or rotating the analysis plane and then to translate and rotate said array, causing said analysis plane to be rotated; and the device includes mapping means designed to calculate at least one parameter describing the propagation of the shear component of the mechanical wave at at least certain points in the viscoelastic medium in order in this way to determine a map of said propagation parameter in the viscoelastic medium.

Other features and advantages of the invention will become apparent over the course of the following description of one of its embodiments, given by way of non-limiting example, in conjunction with the appended drawings.

BRIEF DESCRIPTION OF THE DRAWINGS

In the drawings.

In the various figures, identical references denote identical or similar elements.

DETAILED DESCRIPTION

Figure 1:
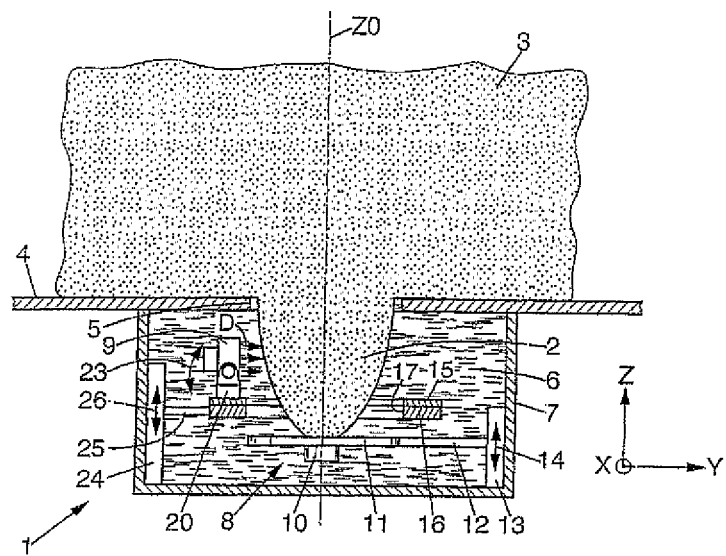
FIG. 1 is a schematic view of an imaging device according to one embodiment of the invention for imaging by shear waves.

The imaging device 1 shown in FIG. 1 is intended for studying the propagation of elastic shear waves in a viscoelastic medium 2 which scatters the ultrasonic compression waves and which may for example be:

an inert body, especially in the case of quality control for industrial applications; or a living being, for example part of the body of a patient, in medical applications.

In the example shown in the drawings, the imaging device 1 is more especially designed for medical imaging of the breast of a female patient 3, the breast therefore constituting the medium 2 to be imaged.

For this purpose, the imaging device 1 may for example include an examination table 4 on which the patient may lie on her stomach. This table is provided with an opening 5 allowing at least one breast 2 of the patient to pass through it, which breast hangs in a bath 6 of ultrasonic coupling agent, for example a gel or liquid, preferably water This liquid bath 6 is bounded by a vessel 7 that also contains an array 9 of ultrasonic transducers and a vibration generator 8 in contact with the breast. The vessel 7 may be transparent, in particular to check that the vibration generator 8 is properly positioned against the breast 2 and that the transducer array 9 is properly positioned alongside the breast.

It should be noted that the examination table 4 may, where appropriate, be designed to allow both the patient's breasts to pass through it, these then hanging in the same liquid bath 6 or in two different baths Therefore the imaging device may be optionally adapted for imaging both breasts of the patient simultaneously.

The vibration generator 8 may comprise an acoustic transducer 10 which generates low-frequency mechanical vibrations in a height-adjustable plate 11, for example positioned in contact with the end of the patient's breast 2 in order to transmit mechanical (elastic) waves thereinto, especially sustained waves comprising a compression component and a shear component. The mechanical waves in question may have for example a frequency between 0.1 Hz and 10 kHz.

It should be noted that the abovementioned mechanical waves could be generated other than by the abovementioned vibration generator, fox example:

- by a transducer generating low-frequency waves and positioned differently against the breast 2; or
- by an array of ultrasonic transducers generating low-frequency mechanical waves remotely by means of time-modulated focused ultrasonic waves using the radiation pressure as for example explained in the abovementioned document WO-A-04/21038 or in document U.S. Pat No. 5,606,971.

In the example shown in FIG. 1, the height of the plate 11 is adjustable, so as to come into contact with the breast 2. This adjustment may optionally be motorized, for example by means of a screw cylinder 13 operated by a sealed electric stepper motor or the like. The cylinder 13 may be connected to the plate 11, for example via a support rod 12, in order to displace the plate 11 and the acoustic transducer 10 in the directions indicated by the double arrow 14, along a vertical axis Z.

Figure 2:
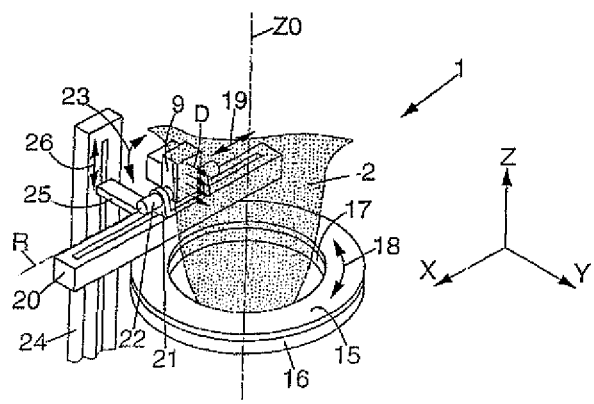
FIG. 2 is a detailed perspective view of part of the device of FIG. 1.

As shown in FIGS. 1 and 2, the array 9 of transducers may for example be in the form of a linear array, in which the transducers are aligned in the vertical plane and are designed to transmit and receive ultrasonic waves, all parallel to the same transmission/detection direction D in a vertical analysis plane (D-Z).

The transducer array 9 may for example be mounted on a rotary platform 15 supported by a fixed platform 16. The two platforms 15, 16 lie in the horizontal plane (X-Y) and are advantageously apertured in order to allow the patient's breast 2 to pass freely through a central passage 17. The rotary platform 15 can be moved angularly with respect to the fixed platform 16, about a vertical central axis Z0, by means of an adjustment system operated by a sealed electric stepper motor (not visible in FIGS. 1 and 2) that may for example be incorporated between the platforms 15 and 16. By moving the rotary platform 15, the analysis plane (D-Z) is therefore rotated, thereby making it possible to image the breast 2 along several points of view, especially for the purpose of reconstructing a three-dimensional image, as will be explained below.

The transducer array 9 may furthermore be able to be moved translationally in the directions indicted by the double arrow 19, perpendicular to the analysis plane (D-Z), in order to image several parallel analysis planes (for example about thirty analysis planes) before said analysis plane is rotated. For this purpose, the array of transducers may for example be mounted so as to slide along the directions 19 on a transverse beam 20 that extends along a direction orthoradially to the central axis Z0 and is fixed to the rotary platform 15. The transducer array 9 moves along the beam 20, for example by means of an adjustment system operated by a sealed stepper motor controlling a nut/screw assembly incorporated into the beam 20.

The transducer array 9 may, where appropriate, be connected to the beam 20 via a swivel 21 which slides along said beam and on which the array 9 can pivot about a rotation axis R parallel to the abovementioned direction 19. It is thus possible, optionally, to vary the direction D in elevation, that is to say to vary the angle of inclination of the direction D to the horizontal plane (X-Y) without varying the analysis plane (D-Z). As will be explained below, this optional movement may also vary the points of view along which the breast 2 is imaged, so as to reconstruct an image thereof in three dimensions.

The pivoting of the transducer array 9 may for example be controlled by a sealed electric stepper motor 22, allowing the array 9 to be displaced in the direction defined by the double arrow 23.

Optionally, the fixed platform 16 may also be able to be moved vertically, in order to image the breast at several heights, especially if the array 9 of transducers is not long enough to cover the desired height of the observation field in the breast 2.

In the example shown, the height of the fixed platform 16 may for example be adjusted by means of a screw cylinder 24 operated by a sealed electric stepper motor or the like, connected to the platform 16, for example by a support rod 25, in order to move the platform 16 in the direction defined by the double arrow 26, along the vertical axis Z.

Figure 3:
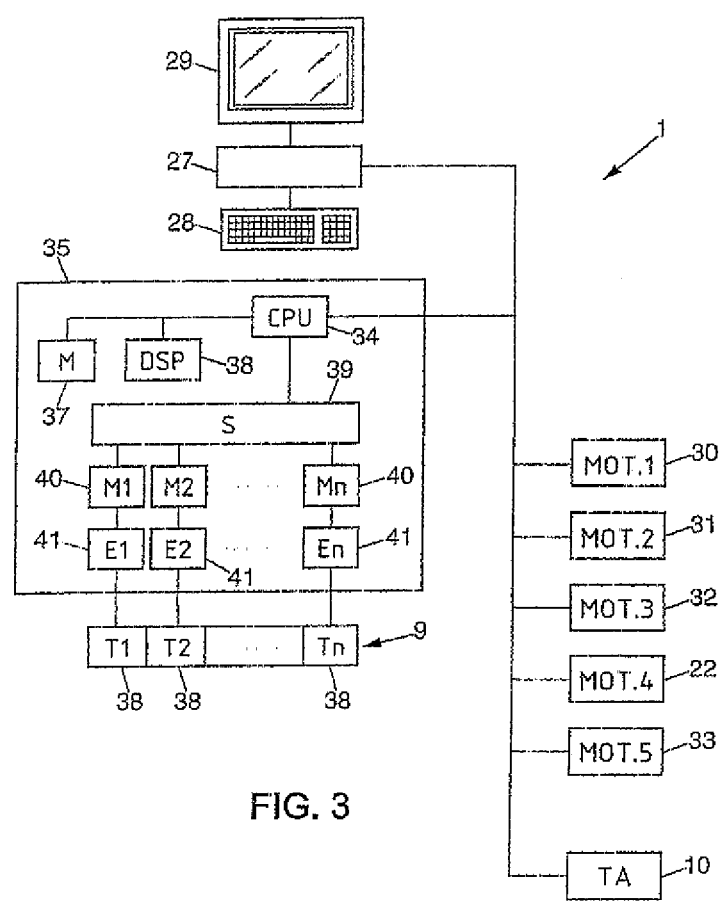
FIG. 3 is a block diagram of the device of FIG. 1.

As shown in FIG. 3, the imaging device may furthermore include a microcomputer 27 (including at least one input interface 28 such as a keyboard or the like, and an output interface 29 such as a screen or the like) or any other electronic central processing unit which controls:

- the acoustic transducer 10 (TA);
- the motor 30 (MOT.1) of the cylinder 13;
- the motor 31 (MOT.2) controlling the rotation of the rotary platform 15;
- the motor 32 (MOT3) controlling the sliding of the transducer array 9 in the direction 19;
- the motor 22 (MOT.4) controlling the pivoting of the transducer array 9 in the direction 23;
- the motor 33 (MOT.5) of the cylinder 24; and
- the electronic central processing unit (CPU) 34 a microprocessor or the like—of an electronic signal processing rack 35.

The central processing unit 34 also controls the n transducers 36 (T1, T2, . . . Tn) of the transducer array 9 (n may for example be 128 or more).

Optionally, the rack 35 may also include:

- a memory 37 (M) connected to the central processing unit 34;
- a specialized circuit 38 (DSP) for processing the signal, also connected to the central processing unit 34;
- a summer 39 (S) connected to the central processing unit 34;
- n memories 40 (M1, M2, . . . Mn) connected to the summer and each assigned to a transducer 36 (each memory 40 may for example have a capacity of 128 Mb or more);
- n samplers 41 (E1, E2, . . . En) interposed between each transducer 36 and the corresponding memory 40.

The device that has just been described operates as follows.

The microcomputer 27 generates sustained elastic mechanical waves in the viscoelastic medium 2 by the acoustic transducer 10 during an excitation step (a).

Moreover, the propagation of the mechanical wave in the viscoelastic medium 2 is observed by echography during an observation step (b) concomitant with the excitation step (a) For this purpose, the microcomputer 27 also causes ultrasonic compression waves to be transmitted (at a frequency for example between 0.5 and 100 MHz, and preferably between 0.5 and 15 MHz, for example around 4 MHz) via the transducers 36 of the array 9.

These compression waves, after they have passed through the coupling gel or liquid 6, penetrate into the medium 2 where they are reflected off scattering particles contained in said medium 2 thereby allowing the movements of the medium 2 to be monitored. The scattering particles in question may consist of any heterogeneity in the medium 2 and especially, when medical application is involved, by collagen particles present in human tissue.

The compression waves thus transmitted may for example be "plane" ultrasonic compression waves (i.e. in this case a wave in which the wavefront is a straight line in the analysis plane (D-Z)) or any other type of focused or unfocused wave clarifying the entire field of observation in the medium 2, for example a wave generated by transmitting random acoustic signals via various transducers 36.

The abovementioned observation step (b) may comprise the following substeps, for each position of the transducer array 9:
(b1) the microcomputer 27 causes the array 9 to transmit a succession of shots of ultrasonic compression waves into the viscoelastic medium 2; and
(b2) the microcomputer 27 causes the array 9 to detect and record, in real time, acoustic signals received from the viscoelastic medium 2, including the echoes generated by the ultrasonic compression waves interacting with the scattering particles of the viscoelastic medium 2, these echoes corresponding (directly or indirectly) to successive images of the movement of the viscoelastic medium, During step (b1), the ultrasonic compression waves are transmitted at a rate of between 10 and 10 000 shots per second and preferably between 10 and 5000 shots per second (this rate is limited by the round-trip time of the compression wave in the medium 2, and therefore by the thickness of the medium 2 in the direction D. This is because it is necessary for all the echoes generated by the compression wave to be received by the probe 36 before a new compression wave is sent).

Each ultrasonic compression wave propagates in the medium 2 with a much higher propagation velocity than the shear waves (for example around 1500 m/s in the human body) and interacts with the scattering particles of the medium 2, thereby generating echoes or other analogue perturbations of the signal, known per se by the term "speckle noise" in the field of echography.

This speckle noise is picked up by the transducers T1 . . . Tn during substep (b2), after each ultrasonic compression wave firing. The signal sij(t) thus picked up by each transducer Ti after the jth firing is firstly sampled at high frequency (for example a frequency ranging from 30 to 100 MHz) and digitized in real time (for example over 12 bits) by the corresponding sampler Ei.

The signal sij(t) thus sampled and digitized is then stored, also in real time, in the corresponding memory Mi.

Again for each position of the transducer array 9, the microcomputer 27 then carries out, generally at a later time, a processing step (c) during which:
(c1) the microcomputer 27 processes the successive acoustic signals received from the viscoelastic medium 2 during substep (b2) in order to determine successive propagation images; and
(c2) the microcomputer 27 determines at least one movement parameter (for example the displacement or the displacement velocity) of the viscoelastic medium 2 at various points in the field of observation.

During substep (b2), after all the signals sij(t) corresponding to a measurement in the same position of the transducer array 9 have been stored, the central processing unit 34 causes these signals to be reprocessed by the summer circuit S (or else said central processing unit itself carries out this processing, or said processing may be carried out in the microcomputer 27) by a conventional beamforming procedure corresponding to substep (c1).

Thus, signals Sj(r,z) each corresponding to the image of the field of observation in the plane (D-Z) after the jth firing are generated.

For example, a signal Sj(t) may be determined by the following formula:

$$Sj(t) = \sum_{i=1}^{n} \alpha_i(r, z) sij[t(r, z) + d_i(d, z)]/Vr$$

where:
sij is the raw signal picked up by the ith transducer after the jth ultrasonic compression wave firing;
t(r,z) is the time taken by the ultrasonic compression wave to reach a point in the field of observation with the coordinates (r,z), where t=0 at the start of the jth firing, r being the abscissa measured in the direction D from an origin and z being the vertical ordinate of the point in question;
di(r,z) is the distance between the point in the field of observation with coordinates (r,z) and the ith transducer, or an approximation of this distance;
V is the average propagation velocity of the acoustic ultrasonic compression waves in the observed viscoelastic medium; and
αi(r,z) is a weighting coefficient taking into account the apodization laws (in practice, it may be considered in many cases that αi(r,z)=1).

After the optional beamforming step, the central processing unit 34 stores the image signals Sj(r,z), where j is the number of the compression wave firing, in a central memory M belonging to the rack 7. These signals may also be stored in the microcomputer 4 when the latter itself carries out the image processing.

These images are processed at a later time or immediately after substep (c2), by correlation and advantageously by intercorrelation, either pairwise or preferably with a reference image which may be:
either a previously determined displacement image, as explained above and used as reference image for the subsequent displacement images (or for a limited number of the subsequent displacement images, for example thirty displacement images);
or an image determined during a preliminary initial observation step (a0), in the same way as the abovementioned successive displacement images, by making the transducer array 9 transmit one or more ultrasonic waves before the excitation step (a) which generates the shear wave (when several ultrasonic compression waves are thus transmitted before the excitation phase, echoes generated by each ultrasonic compression wave interacting with the reflecting particles of the viscoelastic medium are recorded, these echoes corresponding to several successive preliminary images of the viscoelastic medium, and said initial image of the viscoelastic medium is determined by combining said successive preliminary images and in particular by averaging pixel values of said preliminary images).

The abovementioned intercorrelation may for example be carried out in the circuit DSP forming part of the Tack 35 or be programmed in the central processing unit 34 or in the microcomputer 27.

During this intercorrelation process, an intercorrelation function <Sj(x,y), Sj+1(x,y)> for example is maximized so as to determine the displacement undergone by each particle 5 giving rise to an ultrasonic echo.

Examples of such intercorrelation calculations are given in the prior art, especially by O'Donnell et al. ("*Internal displacement and strain imaging using speckle tracking*", IEEE Transactions on Ultrasonics, Ferroelectrics and Frequency Control, Vol. 41, No. 3, May 1994, pp 314-325) and by Ophir et al. ("*Elastography: a quantitative method for imaging the elasticity of biological tissues*", Ultrasonic imaging, Vol. 13, pp 111-134, 1991).

For generalizing the intercorrelation technique using the method proposed by Tanter et al. (M. Tanter, J. Bercoff, L. Sandrin and M. Fink, "*Ultrafast compound imaging for 2D motion vector estimation: Application to transient elastography*", IEEE, Transactions Ultrasonics, Ferroelectrics and Frequency Control 49 (10), pp 1363-1374, 2002), for each position of the transducer array 9, a set of displacement vectors $\vec{u}(\vec{r},t)$ generated by the shear waves at each position $\vec{r}$ in the field of observation in the analysis plane (D-Z) under the effect of the shear wave is thus obtained (these displacement vectors are in two dimensions and have a component along the direction D and a component along the direction Z).

It is also possible to carry out the measurement or to refine the above technique for measuring the displacements (or to enlarge the field of observation) in the analysis plane (D-Z) by carrying out another series of ultrasonic wave shots while modifying the site of the transducer array 9 by pivoting said array about the abovementioned axis R.

Measurement of the displacements is then repeated in several parallel analysis planes (D-Z) by displacing the transducer array 9 into several successive positions along the beam 20 It is thus also possible to measure the displacement, for example in around thirty parallel planes in the case of breast imaging, in a total time of about 1 to 2 s for all the parallel planes.

The platform 15 is then rotated though a predetermined angle and thereby also rotating the analysis plane (D-Z), and the abovementioned operations of measuring displacements in several analysis planes parallel to the new direction D as explained above, are repeated. Displacement fields $\vec{u}(\vec{r},t)$ in two dimensions, with a component along the new direction D and a component along the direction Z, are thus obtained.

After having measured the displacements with at least two orientations of the direction D (for example two orientations at 90° to each other) or where appropriate more than two orientations (for example up to thirty-six angular orientations), a field of displacements $\vec{u}(\vec{r},t)$ in three dimensions in the viscoelastic medium 2 may be reconstructed.

To do this, the values of the displacements, for example along each axis X, Y, Z, as a function of time are collected, where appropriate after temporal resetting of the various measurements (for this purpose, a signal may be transmitted by the transducer 10 with a periodic modulation and the time origin may be taken as one and the same point in the periodic modulation before each sequence of ultrasonic wave shots), and then these values are combined by averages and interpolations to a single field of displacement vectors $\vec{u}(\vec{r},t)$ in three dimensions.

Next, this field of displacements $\vec{u}(\vec{r},t)$ (or another movement parameter) is corrected in order to eliminate therefrom the effects due to the compression component of the elastic mechanical wave generated by the acoustic transducer 10. For this purpose, the curl (rotational) operator is applied to the field $\vec{u}(\vec{r},t)$ in order to determine a vector field $\vec{q}(\vec{r},t)=\overline{\mathrm{rot}}(\vec{u}(\vec{r},t))$.

Thus, only the effects of the shear component of the elastic mechanical wave generated by the acoustic transducer 10 are taken into account.

This set of vectors $\vec{q}(\vec{r},t)$ is stored in the memory M or in the microcomputer 4 and may for example be displayed, especially by means of the screen 4a of the microcomputer, in the form of a slowed-down film where the value of the components of q is illustrated by an optical parameter, such as a gray level or a chromatic level.

Thus, the differences in propagation of the shear wave between the regions of different characteristics in the medium 2, for example the healthy tissue and cancerous tissue in the case of a medical application, may be perfectly displayed.

This shear wave propagation film is furthermore superposable with a conventional echographic image, which may also be generated by the device 1 described above.

Moreover, it is also possible to calculate, not the displacements of each point in the observed medium 2, but the strains of the medium 2, that is to say vectors whose components are the derivatives of the components of the respective displacement vectors with respect to the space variables. These strain vectors can be used, like the displacement vectors, for clearly displaying the propagation of the shear wave in the form of a film and they also have the advantage of factoring out the displacements of the probe 36 relative to the observed medium 2. These strain vectors are processed by applying the curl (rotational) operator to eliminate the effects due to compression component of the elastic mechanical wave generated by the acoustic transducer 10, as explained above in the case of the displacement vectors.

Next, the microcomputer 27 may advantageously carry out a mapping step (d) based on the displacement field or strain field, during which step at least one parameter describing the propagation of the shear waves in the medium 2 is calculated from the variation in the movement parameter (displacement, displacement or strain velocity) processed by applying the curl operator.

The shear wave propagation parameter calculated during the mapping step is for example chosen from: the velocity $C_1$ of the shear waves, the shear modulus μ or the Young's modulus $E(=3\mu)$, the attenuation of the shear waves, the shear elasticity, the shear viscosity ζ, or the mechanical relaxation time of the tissue, or else several of these parameters in the case of an an isotropic medium.

For example, it is possible to calculate the shear modulus μ and the shear viscosity ζ at various points in the field of observation.

To do this, the following propagation equation (1) may be used (assuming that the medium 2 may be considered to a first approximation as a locally homogeneous and isotropic viscoelastic medium), which the displacements $\vec{u}(\vec{r},t)$ generated by the elastic mechanical waves at each position $\vec{r}$ in the medium 2 obey:

$$\rho \partial_t^2 \vec{u} = \mu \nabla^2 \vec{u} + (\lambda+\mu)\nabla(\nabla \vec{u}) + \varsigma \partial_t \nabla^2 \vec{u} + (\xi+\varsigma)\partial_t \nabla(\nabla \vec{u}), \quad (1)$$

where ρ is the density of the medium, μ is the shear modulus (that we seek to reconstruct), λ is the second lamé coefficient, ç is the shear viscosity, taking into account the dissipation into the medium, and ζ is the viscosity of the compression wave. The shear modulus $\mu$ and the second Lamé coefficient $\lambda$ are given, in terms of Young's modulus E and Poisson's ratio $\sigma$ by the equations:

$$\mu = \frac{E}{2(1+\sigma)}, \lambda = \frac{\sigma E}{(1+\sigma)(1-2\sigma)} \tag{2}$$

Each vector field ($\vec{u}$) may be decomposed into an irrotational part ($\vec{u}_I$), an incompressible part ($\vec{u}_T$) and a harmonic part ($\vec{u}_H$) which is both irrotational and incompressible. The harmonic part $\vec{u}_H$ takes into account the global displacements and can therefore be neglected, since here we are studying the case of waves. Using this decomposition, it is possible to show that equation (1) splits into two equations expressing the propagation of the shear waves and of the compression waves with their respective propagation velocities $c_T$ and $c_L$ (ignoring the effect of the viscosity), i.e:

$$\rho \partial_t^2 \vec{u}_T = \mu \nabla^2 \vec{u}_T \qquad c_T = \sqrt{\frac{\mu}{\rho}} \tag{3}$$
$$\rho \partial_t^2 \vec{u}_I = (\lambda + 2\mu)\nabla^2 \vec{u}_I, \qquad c_l = \sqrt{\frac{\lambda + 2\mu}{\rho}}$$

By applying the curl operator to equation (1), a simplified wave equation is thus obtained that no longer contain a contribution from the compression component of the elastic mechanical wave generated by the transducer 10, namely:

$$\rho \partial_t^2 \vec{q} = \mu \nabla^2 \vec{q} + \partial_t \varsigma \nabla^2 \vec{q}, \quad \vec{q} = \nabla \times \vec{u}, \quad \vec{q} \in \mathbb{C}^3 \tag{4}$$

It is then possible to calculate, from equation (4), the parameters $\mu$ and $\zeta$ and the price, now, of third-order spatial derivatives. Equation (4) can be solved simply, for example by being multiplied by the transpose matrix of the system (pseudo-inverse). It is noted that equation (5) represents in fact six equations (three for the real part and three for the imaginary part of $\vec{q}$, in complex notation) for only two unknowns (the density $\rho$ is considered to be constant and equal to that of water).

Thus, in the case of the steady state, with the following notations:

$$q_i^R = A_i \cos(\omega t + \varphi_i)|_{t=0}, \; q_i^I = A_i \cos(\omega t + \varphi_i)|_{t=\pi/(2\omega)}, \tag{5}$$
$$i = x, y, z$$

the available equations may be expressed as:

$$-\rho \omega^2 \begin{pmatrix} q_x^R \\ q_y^R \\ q_z^R \\ q_x^I \\ q_y^I \\ q_z^I \end{pmatrix} = \begin{pmatrix} \nabla^2 q_x^R & \nabla^2 q_x^I \\ \nabla^2 q_y^R & \nabla^2 q_y^I \\ \nabla^2 q_z^R & \nabla^2 q_z^I \\ \nabla^2 q_x^I & -\nabla^2 q_x^R \\ \nabla^2 q_y^I & -\nabla^2 q_y^R \\ \nabla^2 q_z^I & -\nabla^2 q_z^R \end{pmatrix} \begin{pmatrix} \mu \\ \omega \varsigma \end{pmatrix} \tag{6}$$

Multiplication by the transpose matrix gives:

$$-\rho \omega^2 \begin{pmatrix} q_i^R & \nabla^2 q_i^R + q_i^I & \nabla^2 q_i^I \\ q_i^R & \nabla^2 q_i^I - q_i^I & \nabla^2 q_i^R \end{pmatrix} = \tag{7}$$

$$\begin{pmatrix} \nabla^2 q_i^R \nabla^2 q_i^R + \nabla^2 q_i^I \nabla^2 q_i^I & 0 \\ 0 & \nabla^2 q_i^I \nabla^2 q_i^I + \nabla^2 q_i^R \nabla^2 q_i^R \end{pmatrix} \begin{pmatrix} \mu \\ \omega \varsigma \end{pmatrix}$$

with i=x,y,z and the Einstein convention for the identical indices. In the case of the steady state, there is no correlation between $\mu$ and $\zeta$, thereby making it easier to map these two calculated parameters, which are therefore independent of each other.

It should be noted that similar calculations may be used to determine the desired propagation parameters even when the approximation of a locally homogeneous and isotropic medium cannot be made. In this case, a more complex propagation equation is used, namely:

$$\rho \partial_t^2 u_i = \lambda_{iklm} \frac{\partial^2 u_m}{\partial x_k \partial x_l} + \eta_{iklm} \frac{\partial^3 u_m}{\partial_t \partial x_k \partial x_l}, \tag{1'}$$

where $\mu_i$ is the ith component of the displacement vector $\vec{u}(\vec{r},t)$, $\rho$ is the density of the medium 2, $\lambda_{iklm}$ is the elasticity tensor of rank 4, and $\eta_{iklm}$ is the viscosity tensor of rank 4 (using the Einstein convention for the identical indices)

This equation (1') simplifies where the assumption of a transversely isotropic medium, that is to say a medium having fibers aligned in only one direction. In this case the parameters describing the material may be divided into two groups:

one group comprising two shear moduli ($\mu_{\Box}, \mu_{\perp}$) describes the propagation of the shear waves parallel ($\Box$) and perpendicular ($\perp$) to the direction of the fibers; and the other group ($\lambda_c, \lambda_{\perp}, \lambda_M$) describes the propagation of the longitudinal waves (i.e. the compression waves) in the various directions.

The relationship between the strain tensor and the stress tensor is given here by the equation:

$$\begin{pmatrix} \sigma_{xx} \\ \sigma_{yy} \\ \sigma_{zz} \\ \sigma_{yz} \\ \sigma_{xz} \\ \sigma_{xy} \end{pmatrix} = \tag{8}$$

$$\begin{pmatrix} \lambda_{\perp} + 2\mu_{\perp} & \lambda_{\perp} & \lambda_M & 0 & 0 & 0 \\ \lambda_{\perp} & \lambda_1 + 2\mu_{\perp} & \lambda_M & 0 & 0 & 0 \\ \lambda_M & \lambda_M & \lambda_\Box + 2\mu_\Box & 0 & 0 & 0 \\ 0 & 0 & 0 & \mu_\Box & 0 & 0 \\ 0 & 0 & 0 & 0 & \mu_\Box & 0 \\ 0 & 0 & 0 & 0 & 0 & \mu_{\perp} = \frac{C_{11} - C_{12}}{2} \end{pmatrix}$$

$$\begin{pmatrix} u_{xx} \\ u_{yy} \\ u_{zz} \\ 2u_{yz} \\ 2u_{xz} \\ 2u_{xy} \end{pmatrix},$$

where $u_{ik}=\frac{1}{2}(\partial_{x_k}u_i+\partial_{x_i}u_k)$ is the strain tensor and $\sigma_{ik}$ is the stress tensor.

The corresponding propagation equation for the displacement vector u is given by:

$$\rho\partial_t^2 u_i = \frac{\partial \sigma_{ik}}{\partial x_k} + \zeta\partial_i \nabla^2 u_i + \underbrace{(\xi+\zeta)\frac{\partial^3 u_k}{\partial_i \partial x_i \partial x_k}}_{\square 1}, \quad (9)$$

where $\zeta$ is the shear viscosity. The viscosity of the longitudinal waves ($\xi$) may be neglected at relatively low frequencies (in the Hz or kHz range) In addition, $\nabla u$ has a low value owing to the value of the Poisson's ratio. Thus $\xi$, $\zeta$ and $\nabla u$ have low values and the third part on the right-hand side of equation 9 can therefore be legitimately neglected Putting equation 8 into equation 9 gives:

$$\rho\partial_t^2 u = \mu_\perp \nabla^2 u + (\lambda+\mu_\perp)\nabla(\nabla u) + \tau\begin{pmatrix}\frac{\partial^2 u_x}{\partial z^2}+\frac{\partial^2 u_z}{\partial x \partial z} \\ \frac{\partial^2 u_y}{\partial z^2}+\frac{\partial^2 u_z}{\partial y \partial z} \\ \nabla^2 u_z + \partial_z(\nabla u)\end{pmatrix} + \zeta\partial_i\nabla^2 u, \quad (10)$$

with the notation $\tau=\mu_{\parallel}-\mu_\perp$ and assuming that all the elastic moduli of the longitudinal waves are equal, i.e. $\lambda=\lambda_{\parallel}=\lambda_\perp=\lambda_M$.

After application of the curl operator, the following equation is obtained:

$$\rho\partial_t^2 q = \mu_\perp \nabla^2 q + \tau\nabla \times \begin{pmatrix}\frac{\partial^2 u_x}{\partial z^2}+\frac{\partial^2 u_z}{\partial x \partial z} \\ \frac{\partial^2 u_y}{\partial z^2}+\frac{\partial^2 u_z}{\partial y \partial z} \\ \nabla^2 u_z + \partial_z(\nabla u)\end{pmatrix} + \varsigma\partial_i\nabla^2 q \quad (11)$$

This equation (11) gives in fact six equations that can be used in particular to calculate $\mu_\perp$, $\tau$ and $\zeta$.

It should be noted that the invention is applicable whatever the method of measuring the movement parameter (displacement or the like) of the medium 2. This parameter would thus be, where appropriate, determined by MRI.

The method that has just been described could also be coupled with acoustooptic imaging of the medium 2, as described for example in document WO-A-04/85978.

The invention claimed is:

1. An elastography imaging method,
   wherein the elastography imaging method generates a sustained non-ultrasound mechanical wave having a shear component and a compression component in a viscoelastic medium,
   wherein the elastography imaging method determines at least one movement parameter describing the movement of the viscoelastic medium at various points in a propagation of the mechanical wave,
   wherein the elastography imaging method includes at least one observation step during which the propagation of the mechanical wave at a multitude of points in the viscoelastic medium is observed by a technique selected from the group consisting of ultrasound echography imaging and magnetic resonance imaging (MRI), and
   wherein the elastography imaging method includes a correction step during which the movement parameter is processed to calculate a curl thereof so as to remove the effects due to the compression component of said mechanical wave and to take into account only the effects due to the shear component of the mechanical wave.

2. The imaging method as claimed in claim 1, in which the at least one observation step comprises the following substeps:
   a succession of shots of ultrasonic compression waves are transmitted into the viscoelastic medium at a rate of at least ten shots per second by an array of transducers controlled independently of one another; and
   successive acoustic signals received from the viscoelastic medium, including the echoes generated by the ultrasonic compression waves interacting with the viscoelastic medium, are detected and recorded in real time.

3. The imaging method as claimed in claim 2, which furthermore includes at least one processing step during which:
   the successive acoustic signals received from the viscoelastic medium are processed in order to determine successive propagation images of the mechanical wave; and
   said movement parameter of the viscoelastic medium is determined at various points from said successive propagation images.

4. The imaging method as claimed in claim 1, in which several successive propagation images of the mechanical wave in the viscoelastic medium are produced along several points of view and the successive propagation images are combined in order to determine a vector value of said movement parameter.

5. The imaging method as claimed in claim 4, in which a three-dimensional vector value of said movement parameter is determined.

6. The imaging method as claimed in claim 4, in which, in order to produce the successive propagation images of the mechanical wave along several points of view, a linear array of ultrasonic transducers is used that transmits and detects the ultrasonic compression waves along a transmission/detection direction in an analysis plane and said linear array is displaced outside the viscoelastic medium, causing said analysis plane to be rotated.

7. The imaging method as claimed in claim 6, in which the linear array is displaced by moving translationally, without the analysis plane being rotated, and then said linear array is rotated, causing said analysis plane to be rotated.

8. The imaging method as claimed in claim 7, in which the transmission/detection direction of the transducers of the linear array is varied without either translating or rotating the analysis plane, and then said linear array is translated and rotated, causing said analysis plane to be translated and rotated.

9. The imaging method as claimed in claim 1, in which said movement parameter is chosen from a displacement, a displacement velocity and a stress of the viscoelastic medium.

10. The imaging method as claimed in claim 1, which furthermore includes a mapping step during which at least one propagation parameter describing the propagation of the shear component of the mechanical wave at at least certain points in the viscoelastic medium is calculated, from a variation of the movement parameter over time, in order to determine a map of said at least one propagation parameter in the viscoelastic medium.

11. The imaging method as claimed in claim 10, in which the at least one propagation parameter of the shear component of the mechanical wave, which is calculated during the mapping step, is chosen from velocity of the shear component of the mechanical waves, a shear modulus, a Young's modulus, an attenuation of the shear component of the waves, shear elasticity, shear viscosity and mechanical relaxation time, or several of these parameters in the case of an anisotropic medium.

* * * * *